(12) United States Patent
Gil et al.

(10) Patent No.: US 8,317,793 B2
(45) Date of Patent: Nov. 27, 2012

(54) CUTTING INSTRUMENT AND METHOD OF USE FOR PREPARING AN OSTEOCHONDRAL PLUG FOR IMPLANTATION

(75) Inventors: Carlos E. Gil, Collierville, TN (US); Jeetendra Subhash Bharadwaj, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 116 days.

(21) Appl. No.: 13/027,313

(22) Filed: Feb. 15, 2011

(65) Prior Publication Data
US 2011/0137315 A1 Jun. 9, 2011

Related U.S. Application Data

(62) Division of application No. 11/734,811, filed on Apr. 13, 2007, now Pat. No. 7,955,336.

(51) Int. Cl.
*A61B 17/00* (2006.01)
(52) U.S. Cl. ........................................ 606/79
(58) Field of Classification Search ............... 606/79
See application file for complete search history.

(56) References Cited

U.S. PATENT DOCUMENTS

| | | | |
|---|---|---|---|
| 3,296,704 A | 1/1967 | Zajkowski | |
| 4,416,278 A | 11/1983 | Miller | |
| 4,718,413 A | 1/1988 | Johnson | |
| 5,356,414 A | 10/1994 | Cohen et al. | |
| 5,437,675 A | 8/1995 | Wilson | |
| 5,540,692 A | 7/1996 | Tidwell | |
| 5,616,146 A | 4/1997 | Murray | |
| 5,683,400 A | 11/1997 | McGuire | |
| 6,065,909 A | 5/2000 | Cook | |
| 6,676,662 B1 | 1/2004 | Bagga et al. | |
| 6,875,222 B2 | 4/2005 | Long et al. | |
| 6,962,592 B2 | 11/2005 | Gattuma et al. | |
| 2003/0139815 A1 | 7/2003 | Grooms et al. | |
| 2005/0149040 A1 | 7/2005 | Haines et al. | |
| 2007/0173852 A1* | 7/2007 | Gil et al. ................ | 606/87 |

OTHER PUBLICATIONS

U.S. Appl. No. 11/339,694, Inventor: Carlos E. Gil; Title: A Device for Trimming an Osteochondral Implant and a Surgical Procedure Involving Same.

* cited by examiner

*Primary Examiner* — Kevin T Truong
*Assistant Examiner* — David Bates

(57) ABSTRACT

A cutting instrument and method of use for preparing an osteochondral plug for implantation into a bone defect site. The instrument includes a dual function cutting block, a base holder, a rod mechanism and a trimming mechanism. The cutting block has a bore sized to receive the plug, at least one trimming channel and a transverse paring slot. The cutting block functions to hold the plug within the bore to allow for length and cross-sectional sizing. The base holder is constructed to fix the cutting block in a first orientation that allows the rod mechanism to position the plug within the cutting block for accurate length sizing. The base holder is also constructed to fix the cutting block in a second orientation which aligns the cutting block with the trimming mechanism so that an angled blade may engage the trimming channel and cut at least two sides of the plug.

7 Claims, 10 Drawing Sheets

CUTTING INSTRUMENT AND METHOD OF USE FOR PREPARING AN OSTEOCHONDRAL PLUG FOR IMPLANTATION

CROSS REFERENCE TO RELATED APPLICATION

This application is a divisional application of U.S. patent application Ser. No. 11/734,811, filed Apr. 13, 2007.

TECHNICAL FIELD

The present invention relates generally to the field of surgery and osteochondral grafting, and more particularly, to ancillary operating room instruments and methods for cutting and trimming an osteochondral bone plug for implantation into a host bone defect site of a patient.

BACKGROUND OF THE INVENTION

Human joint surfaces are covered by articular cartilage that provides a resilient, durable surface with low friction. Cartilage is an avascular tissue that has a small number of chondrocytes encapsulated within an extensive extracellular matrix. The cartilage acts to distribute mechanical forces and to protect subchondral bone. The knee is a particular instance of a cartilage surfaced (the condyle) bone area. The knee comprises three bones—the femur, tibia, and patella that are held in place by various ligaments. Corresponding chondral areas of the femur and the tibia form a hinge joint and the patella acts to protect the joint. Portions of the chondral areas as well as the undersurface of the patella are covered with articular cartilage that allows the femur, patella and tibia to smoothly glide against each other without causing damage.

Damage to the articular cartilage, subchondral bone or both can result from traumatic injury or a disease state. For example, articular cartilage in the knee can be damaged due to traumatic injury as with athletes and via a degenerative process as with older patients. The knee cartilage does not heal well due to the lack of vascularity. Hyaline cartilage in particular has a limited capacity for repair and lesions in this material, without intervention, can form scar tissue lacking the biomechanical properties of normal cartilage.

A number of procedures are used to treat damaged articular cartilage. Currently, the most widely used procedure involves lavage, arthroscopic debridement and repair stimulation. Repair stimulation is conducted by several methods including, drilling, abrasion arthroplasty and microfracture. The goal of these procedures is to penetrate into subchondral bone to induce bleeding and fibrin clot formation. This reaction promotes initial repair. However, the resulting formed tissue is often fibrous in nature and lacks the durability of normal articular cartilage.

Another known treatment involves the removal and replacement of the damaged articular cartilage with a prosthetic device. However, historically, artificial prostheses have largely had limited success since they are non-elastic, and therefore lack the shock-absorbing, properties characteristic of the normal cartilage. Moreover, the known artificial devices have shown a reduced ability to withstand the high and complex forces inherent to routine knee joint function.

In an attempt to overcome the problems associated with the above techniques, osteochondral transplantation, also known as "mosaicplasty" or "OATS" has been used to repair articular cartilage. This procedure involves removing injured tissue from the articular defect and drilling cylindrical openings in the area of the defect and underlying bone. Cylindrical plugs, consisting of healthy cartilage overlying subchondral bone, are harvested from another area of the patient, typically from a lower weight-bearing region of the joint under repair, or from a donor patient, and are implanted in the host openings. However, in these cases, if the opening is too large, the graft can rotate or move within the host site and become loose, which will prevent bio-integration with the surrounding tissues. Further, if the host site is too small, significant tissue and cellular damage can occur to the graft during the implantation.

Historically, osteochondral grafting has been used successfully to repair chondral damage and to replace damaged articular cartilage and subchondral bone. First, in this procedure, cartilage and bone tissue of a defect site are removed by routing to create a cylindrical bore of a precise geometry. Then a cartilage and subchondral bone plug graft is harvested in a matching geometry. The donor plug graft is typically removed from another body region of less strain. The donor plug graft can be harvested from a recipient source (autograft) or from another suitable human or other animal donor (allograft). The harvested plug graft is then implanted into the bore of the routed defect site. Healing of the plug graft to the host bone results in fixation of the plug graft to the surrounding host region.

Success of the grafting process is dependant on the intimate seating and sizing of the graft within the socket. First, surface characteristics of the plug graft are critical. For the procedure to be successful, the surface of the transplanted plug graft must have the same contour as the excised osteochondral tissue. If the contour is not a correct match, a repaired articular surface is at risk for further damage during motion. Additionally, some graft shapes do not pack well into irregular defects. The graft may have a propensity to rotate resulting in poor integration of the graft to the surrounding host tissue. An improperly placed and sized plug graft can result in host tissue integration failure and post implantation motion.

Since the plug graft is press-fit within a host site, accurate sizing of the plug graft is critical to the success of the implanted graft material. Hence, a surgeon must accurately cut and trim the plug graft to size in order to ensure a proper press fit within the recipient host site. If the plug graft is too small or too large or otherwise incorrectly sized, the plug graft may be damaged upon implantation or damage the host site when inserted. Extraction procedures and tools can cause further damage to the boundary host site cells and to the graft structural integrity.

Thus, there is a need for a multi-functioning "back table" cutting instrument in which a donor plug graft may be secured and that allows for accurate length cutting and cross-sectional trimming without causing damage to the donor plug graft prior to implantation.

SUMMARY OF THE INVENTION

The present invention comprises a cutting instrument and method for use in preparing an osteochondral plug for implantation in a bone defect within the body. The instrument and method disclosed herein employs a dual function cutting block that provides the operator with two cutting mechanisms within one instrument. The cutting instrument is to be readily utilized to accurately pare the length and cut the cross-section profile of the osteochondral plug. Further, the dual function cutting block approach provides for two preparation procedures to be performed on the osteochondral plug without the plug being removed from the protective cutting block.

More particularly, the present invention provides in one aspect, a cutting instrument for preparing an osteochondral plug for implantation within a bone defect site. The cutting instrument includes a dual function cutting block having a bore sized to receive an osteochondral plug, with the cutting block being configured to first function to hold the osteochondral plug within the bore to allow for length sizing. The cutting block is further configured to function to hold the osteochondral plug within the bore to allow for cross-sectional sizing of the osteochondral plug. The cutting instrument includes further a base holder configured for selectively engaging the cutting block in a first orientation or a second orientation. The cutting instrument also has a trimming mechanism for cutting the osteochondral plug to fit within a bone defect site. The trimming mechanism is attached to the base holder and aligned with the bore of the cutting block when the cutting block is positioned in the second orientation so when used, the trimming mechanism cuts the osteochondral plug.

The present invention provides in another aspect, a cutting instrument for preparing an osteochondral plug for implantation within a bone defect site. The cutting instrument includes a dual function cutting block having a first end and a second end with a longitudinal bore sized to receive an osteochondral plug extending at least partially between the first end and second end. The cutting block also includes a paring slot formed intermediate the first end and second end and positioned transverse to the longitudinal bore. The cutting block has at least one trimming channel extending from the first end to the second end of the cutting block and is substantially parallel to the longitudinal bore. The at least one trimming channel is further configured for receiving a trimming mechanism. In use, the cutting block functions to hold the osteochondral plug within the bore to allow for length sizing and cross-sectional sizing. The cutting instrument will also include a base holder that holds the cutting block in either a first orientation or a second orientation. Further, the cutting instrument has a rod mechanism for adjusting the position of the osteochondral plug in the longitudinal bore relative to the paring slot when the cutting block is positioned in the first orientation. The osteochondral plug is able to be slidingly positioned within the longitudinal bore and pared to a predetermined length by a cutting blade inserted into the paring slot. Also included in the cutting instrument is a trimming mechanism for cutting the osteochondral plug to a predetermined cross-sectional size. The trimming mechanism is attached to the base holder and aligned with the longitudinal bore of the cutting block and the at least one trimming channel so when the cutting block is positioned in the second orientation, the trimming mechanism will be inserted into the at least one trimming channel and cut the osteochondral plug to a predetermined cross-sectional size.

Another aspect of the present invention provides a method for preparing an osteochondral plug for implantation, the method includes obtaining a cutting instrument having a dual function cutting block with first and second ends, with a longitudinal bore sized to receive the osteochondral plug extending at least partially between these ends. The cutting block also has a transverse paring slot formed intermediate the first and second ends for cutting the osteochondral plug to a certain length size, and further includes at least one trimming channel that extends from the first end to the second end of the cutting block and is substantially parallel to the longitudinal bore. The trimming channel is configured to receive a trimming mechanism for cross-sectional sizing of the osteochondral plug. Also included in the cutting instrument is a base holder that can hold the cutting block in a first orientation and a second orientation. Further, the cutting instrument has a rod mechanism for adjusting the position of the osteochondral plug in the longitudinal bore relative to the paring slot so when the cutting block is positioned in the first orientation, the end of the threaded rod will contact the osteochondral plug. The threaded rod when rotated, will engage the base holder causing the end to move and adjust the position of the osteochondral plug relative to the paring slot. In addition, the cutting instrument has a trimming mechanism for cutting the osteochondral plug to a predetermined cross-sectional size. The trimming mechanism is attached to the base holder and aligned with the longitudinal bore and the at least one trimming channel of the cutting block when the cutting block is positioned in the second orientation. The trimming mechanism will cut the osteochondral plug to a predetermined cross-sectional size when it enters the at least one trimming channel. The method also includes inserting the osteochondral plug into the longitudinal bore of the cutting block at the first end of the cutting block. The method includes further positioning the cutting block to the first orientation. The method includes further yet slidingly positioning the inserted osteochondral plug relative to the paring slot by threadably advancing the rod mechanism relative to the base holder and cutting block. The method may also include paring the osteochondral plug to a predetermined length by using a cutting blade inserted into the paring slot.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

BEST MODE FOR CARRYING OUT THE INVENTION

Generally stated, disclosed herein is a cutting tool and a method of use for preparing an osteochondral plug (for example) for implantation into a bone defect located in the distal aspect of a femoral condyle (for example).

One embodiment of a cutting instrument 10, in accordance with an aspect of the present invention, is illustrated in FIGS. 1-4 and described below.

Figure 1:
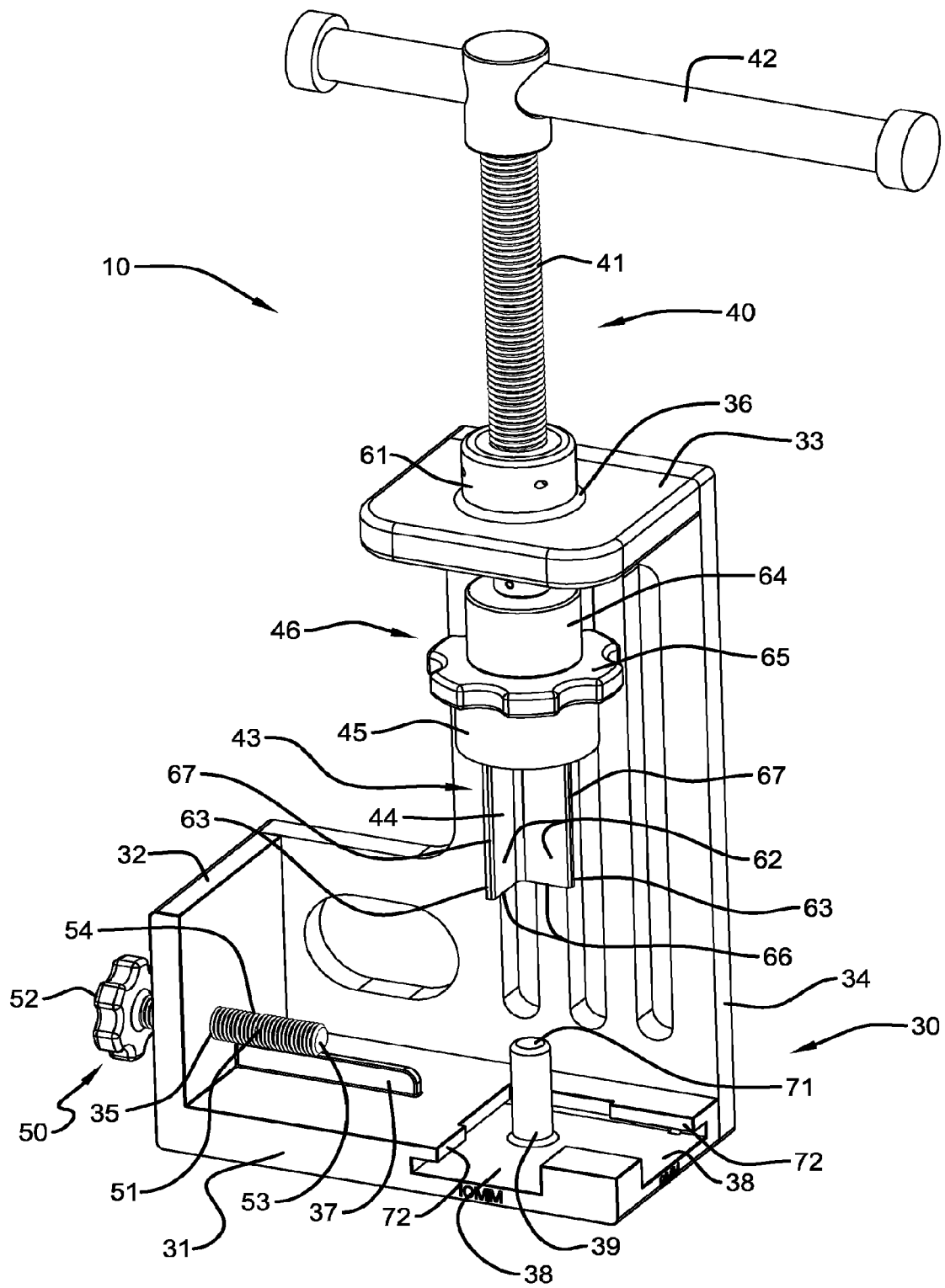
FIG. 1. is an isometric view of one embodiment of a cutting instrument, shown with an assembled trimming mechanism and rod mechanism, in accordance with an aspect of the present invention.

As shown in FIG. 1, cutting instrument 10 includes a base holder 30, a trimming mechanism 40, a rod mechanism 50 and a cutting block 20 (see FIG. 2), base holder 30 consists of a base plate 31 and a back plate 34. Integrally attached to base plate 31 and back plate 34 is a side bracket 32. A horizontally oriented threaded hole 35 extends through side bracket 32. A top bracket 33 may be integrally attached to back plate 34 and may include a vertically oriented hole 36 extended therethrough. Base plate 31 may also include a retention flange 37 that is positioned to contact and maintain a first orientation of a cutting block (not shown) which will be used for trimming the osteochondral graft (not shown) to the appropriate length. It should be noted that the terms osteochondral graft and osteochondral plug as used herein are intended to pertain to the same biologic implant and may be used interchangeably. FIG. 1 also shows a trimming post 39 located within an alignment slot 38 disposed within the top surface of base plate 31. Trimming post 39 is positioned substantially perpendicular to and fixed to base plate 31, with an upper end 71 being configured to contact on osteochondral graft without causing damage to the cartilaginous end of the graft. Alignment slot 38 extends from two adjacent edges of base plate 31 to form an angular junction. As shown in FIGS. 1-4, a peripheral retention lip 72 also extends for a portion of each alignment slot 38 extension. The functionality of peripheral retention lip 72 is to secure cutting block 20 within alignment slot 38 (see FIG. 4) and maintain cutting block 20 in a second orientation relative to base holder 30.

As seen in FIGS. 1-4, cutting tool 10 further include trimming mechanism 40 that functions to cut or trim an osteochondral graft to a predetermined cross-sectional size and shape. Trimming mechanism 40 is constructed of a threaded rod 41 having two distinct ends. Attached to a first end is a T-handle 42 that is used to rotate threaded rod 41. Threaded rod 41 engages a threaded bushing assembly 61 that is fixed within hole 36 that extends through top bracket 33. Bushing assembly 61 is constructed to threadingly engage threaded rod 41 while allowing the length of threaded rod 41 to, in a controlled manner, pass through top bracket 33. Attached at the second end of threaded rod 41 is a coupling assembly 46. Coupling assembly 46 prevents the cutting assembly 43 from rotating when threaded rod 41 is threaded through bushing assembly 61. The mechanical functioning of threaded rod 41 and bushing assembly 61 results in a unidirectional, single action cutting motion of trimming mechanism 40. The single action cutting motion of trimming mechanism 40 is beneficial to the user because no heat is generated at the angled blade-osteochondral graft interface, therefore adjacent tissue is preserved and remains viable for post-operative ingrowth. Further, the single action cutting motion more accurately resects the bone tissue, therefore a more intimate fit results between the osteochondral graft and the host site.

Figure 2:
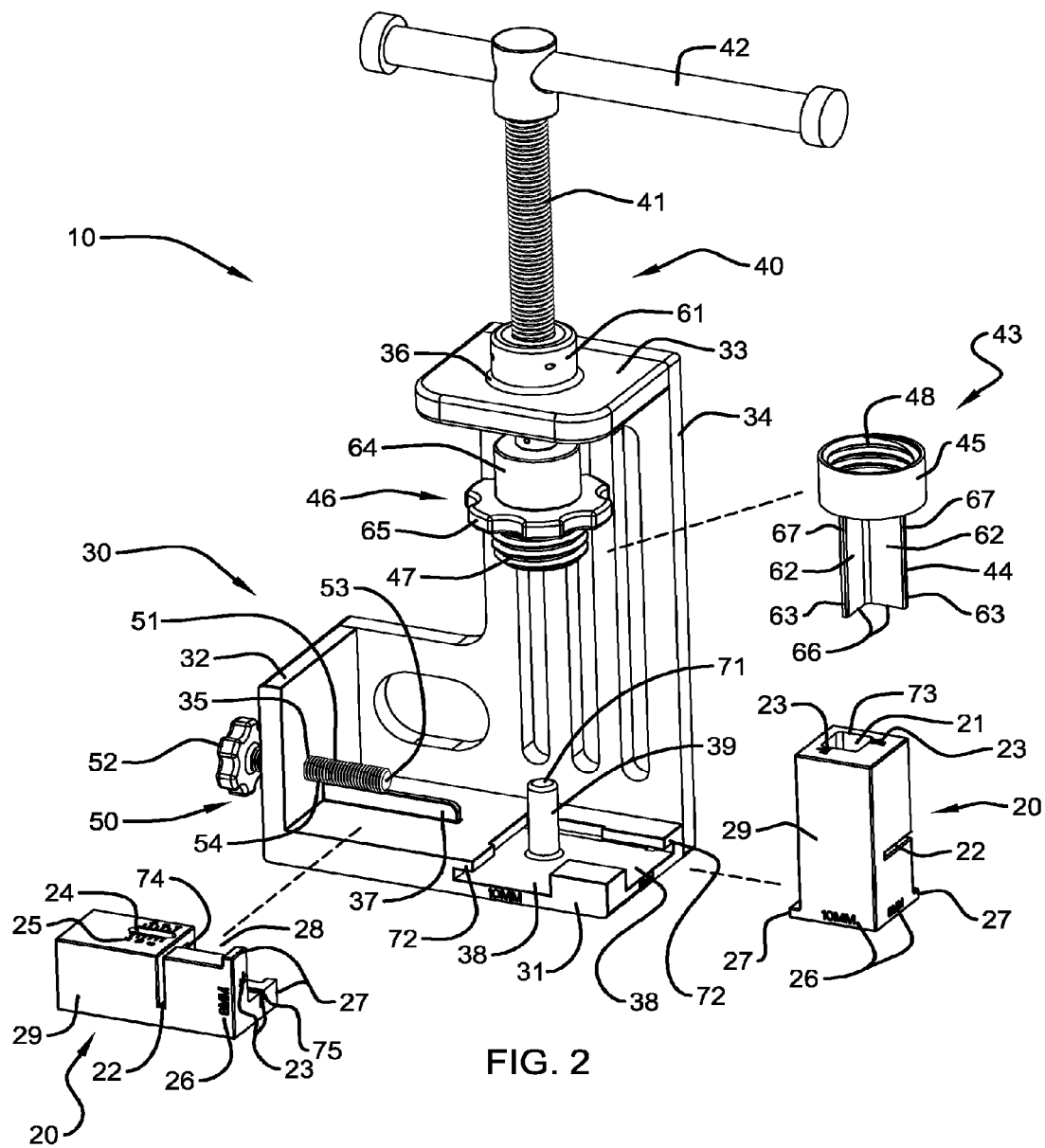
FIG. 2 is an isometric, exploded view of the cutting instrument of FIG. 1, with two cutting blocks shown prior to insertion in two orientations, in accordance with an aspect of the present invention.
Figure 3:
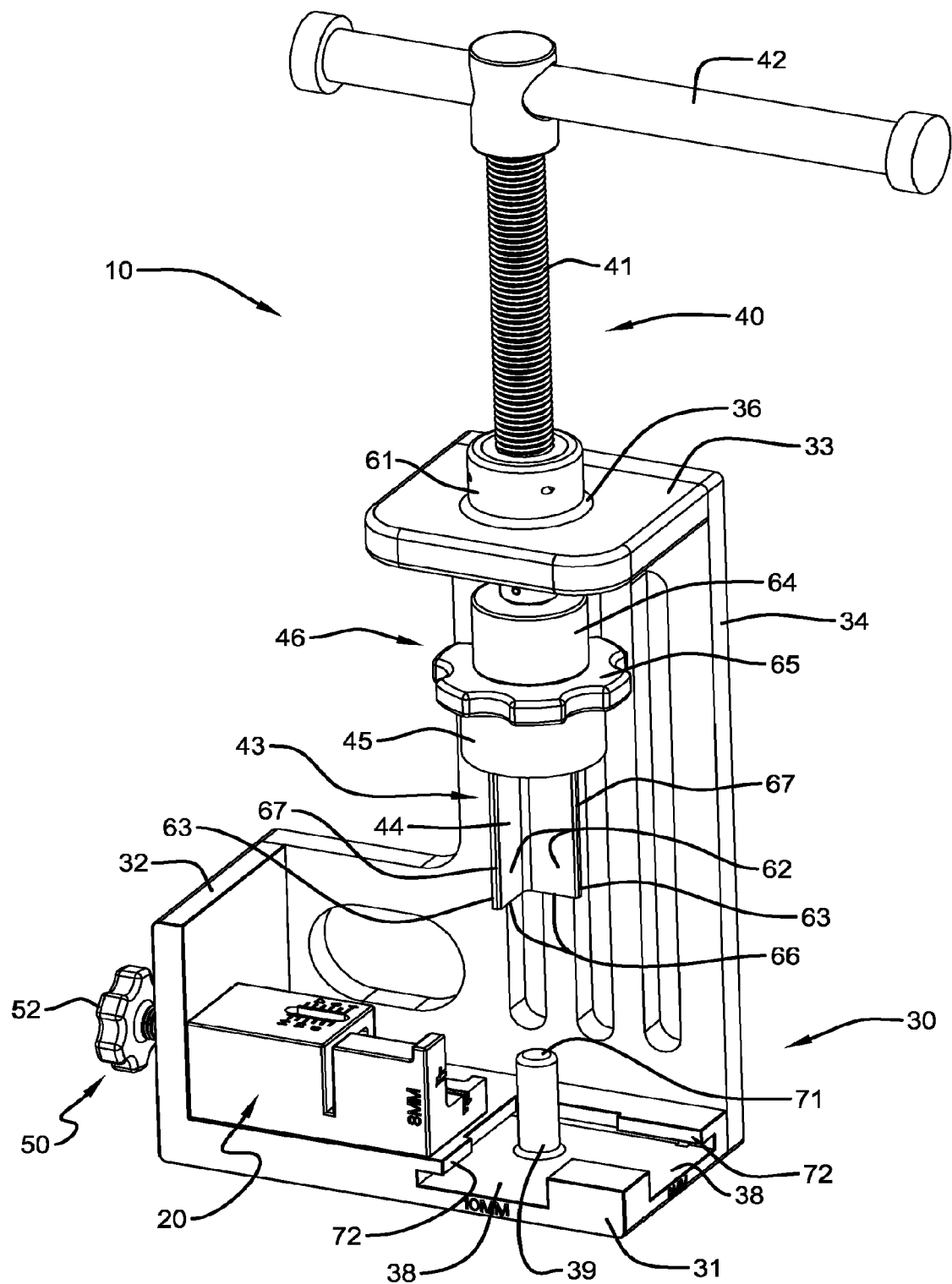
FIG. 3 is an isometric view of the cutting instrument of FIG. 1, shown with a cutting block positioned in a first orientation that is adjacent to a base plate of a base holder and a retention flange, in accordance with an aspect of the present invention.

Coupling assembly 46 as shown in FIG. 2 includes generally a connecting member 64 that is rotatably fixed to the second end of threaded rod 41 and a knob 65 integrally connected to an externally threaded member 47. Coupling assembly 46 functions to secure cutting assembly 43 to trimming mechanism 40 in a manner that facilitates expeditious exchange of various sizes and configurations of cutting assembly 43 and permits cutting assembly 43 to remain motionless while threaded rod 41 is rotated. For example purposes only, the method of securement as shown in FIG. 2, may include a threaded member 47 being configured to engage with threaded connector member 45 of cutting assembly 43.

Figure 6:
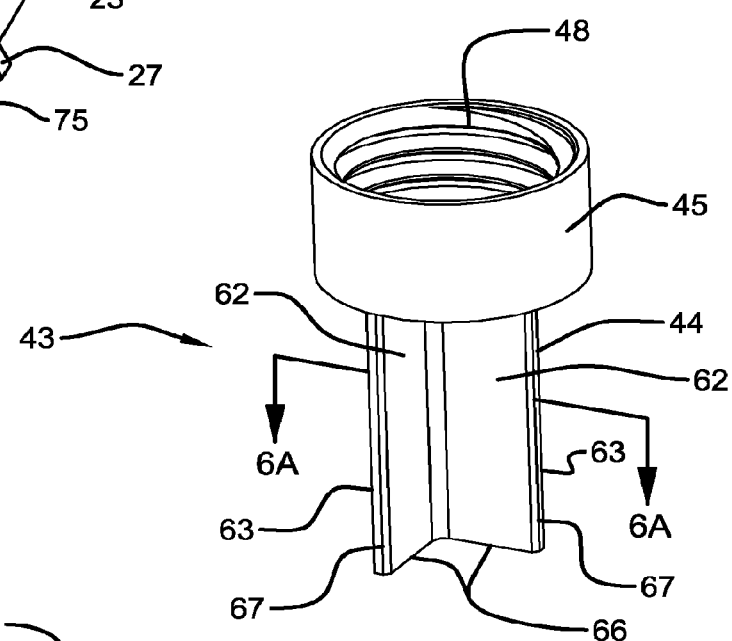
FIG. 6 is an isometric view of a cutting assembly, in accordance with an aspect of the present invention.
Figure 6A:
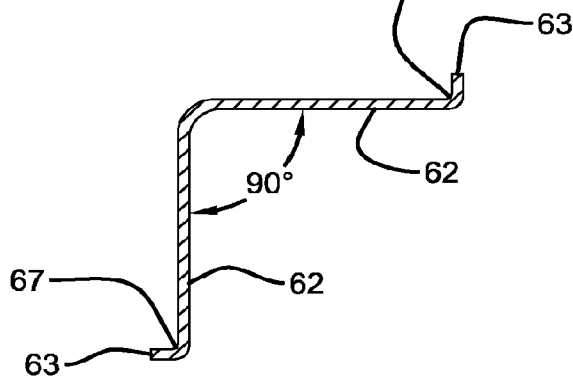
FIG. 6A is cross-sectional, end elevational view of the angled blade component of the cutting assembly of FIG. 6 taken along line 6A-6A, in accordance with an aspect of the present invention.

As depicted in FIGS. 2 and 6, cutting assembly 43 includes threaded connector member 45 and an angled blade 44. In the example shown, angled blade 44 includes two cutting members 62 that are joined together to resect or trim two sides of an osteochondral graft. For the example shown, each cutting member 62 is configured as a relatively rectangular shaped bar with a cutting edge 66, and two outside edges of 67. As seen in FIGS. 6 and 6A, cutting members 62 are joined together an angle of about ninety degrees. It should be understood to those skilled in the art that the angle at which cutting members 62 are joined herein is for example purposes only and that many other angular configurations may be considered for use in cutting instrument 10. Further, angled blade 44 as shown will generally, when used, cut two sides of an osteochondral graft. It should be understood to those skilled in the art that it is contemplated that the number of sides trimmed may be varied by modifying the number and orientation of the cutting members used in constructing the angled blade element. Cutting edges 66 for each cutting member 62 are oriented substantially parallel relative to each other and lie within the same horizontal plane. To assist in ensuring proper alignment of angled blade 44 within cutting block 20 and also provide structural rigidity, outside edges 67 each are configured to include a flange 63 (see FIG. 6A) that extends generally, the full length of cutting member 62.

FIGS. 1-4 depict cutting tool 10 to include further rod mechanism 50 that functions to position an osteochondral graft relative to cutting block 20 so as to allow an operator to pare the graft to a certain overall length. Rod mechanism 50 is constructed of a threaded rod 51 with a knob 52 fixed to one end that is used to rotate and cause threaded rod 51 to axially translate. The opposite end of threaded rod 51 is configured to function as a plug pusher end 53 with the surface of the end being configured to contact the osteochondral graft without causing structural damage to the articular cartilage of the graft. The external threads 54 of threaded rod 51 will engage with the internal threads (not shown) of horizontally oriented threaded hole 35 of side bracket 32 to provide for controlled translational motion. As seen in FIG. 7B, rod mechanism 50 when engaged, will slidingly push the osteochondral graft relative to the paring slot 22 of cutting block 20 while cutting block 20 is positioned in a first orientation as to base holder 30.

As discussed previously and as shown in FIGS. 2, 3 and 4, cutting tool 10 also includes cutting block 20. FIG. 5 depicts cutting block 20 to generally consist of a body member 29 having a continuous longitudinal bore 21 formed therein for receiving a harvested osteochondral graft (not shown). In the example shown, bore 21 has a square cross-section which corresponds to the cross-section of the harvested graft, although it should be understood to those skilled in the art that the graft may have a cross-sectional profile of a different configuration or shape, including, but not limited to triangular, hexagonal, rectangular or circular. One end of body 29 and bore 21 serves as an inlet 73 (see FIGS. 7D and 7E) for receiving an osteochondral plug. A measurement port 24 is disposed on one of the sides of body member 29 that allows the user to visualize the graft within bore 21. Length indicia 25 are also disposed adjacent to port 24 to provide the user with the ability to accurately maneuver rod mechanism 50 and adjust the inserted graft to the correct predetermined length marking prior to paring. Positioned adjacent to the outlet 74 of bore 21 is paring slot 22 that is oriented transverse to body 29 and extends the entire cross-section. Paring slot 22 is a spaced relation to length indicia 25 to allow the user to accurately pare the graft in a manner to be described below.

As seen in FIG. 5, at least two sides of body 29 are removed adjacent to outlet 74 resulting in an access cutaway 28. Cutaway 28 is configured to permit cutting block 20 to be positioned in a second orientation relative to base holder 30. When placed into the second orientation, trimming post 39 is partially enclosed by cutaway 28 as cutting block 20 is slid into alignment slots 38. Extending radially from at least two sides of the second end of body 29 are alignment tabs 27 that are sized and configured to be secured by corresponding retention lips 72 (see FIG. 4) following final placement of cutting block 20 in the second orientation.

Figure 4:
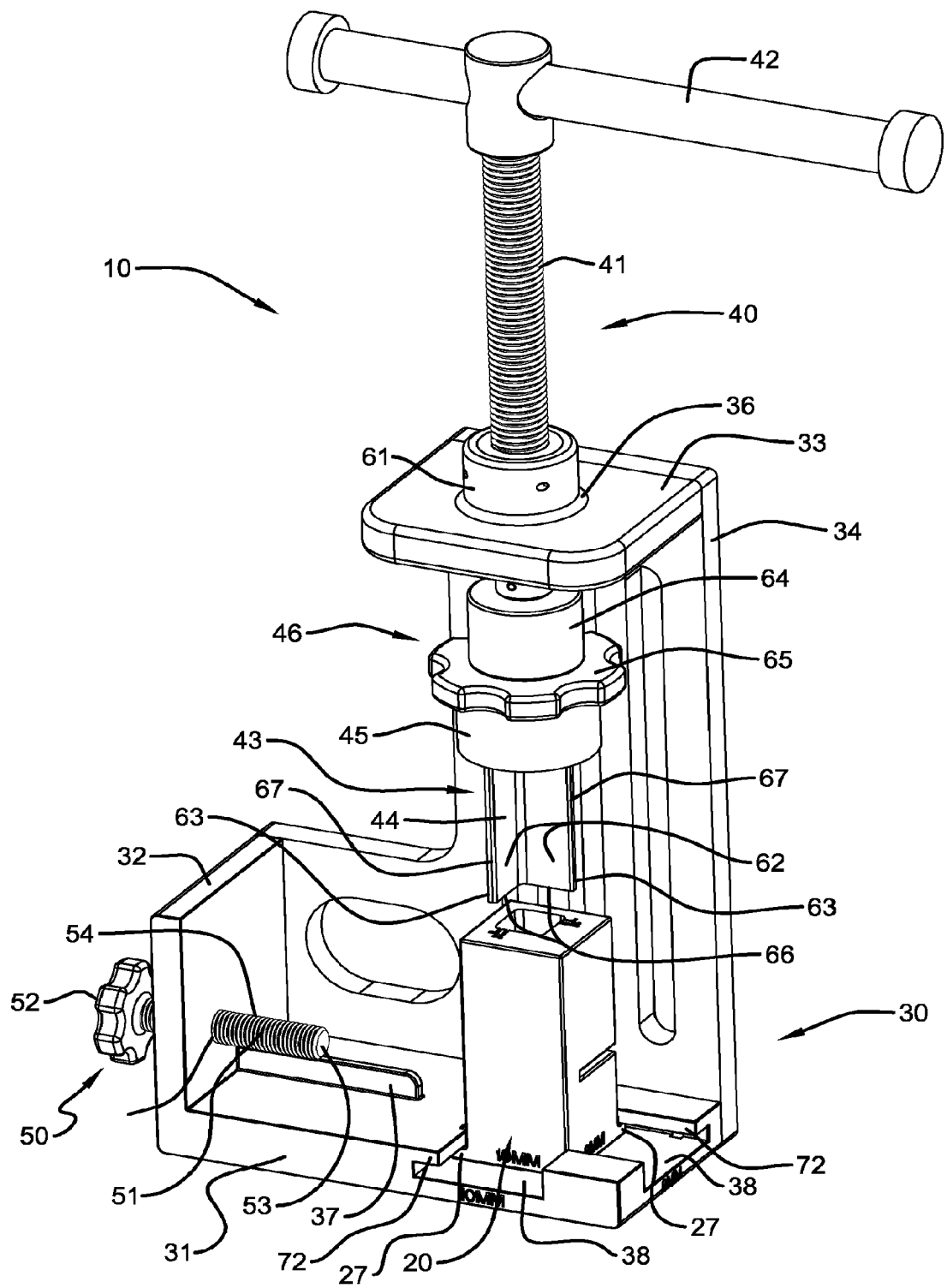
FIG. 4 is an isometric view of the cutting instrument of FIG. 1, shown with the cutting block positioned in a second orientation following engagement with an alignment slot, in accordance with an aspect of the present invention.
Figure 5:
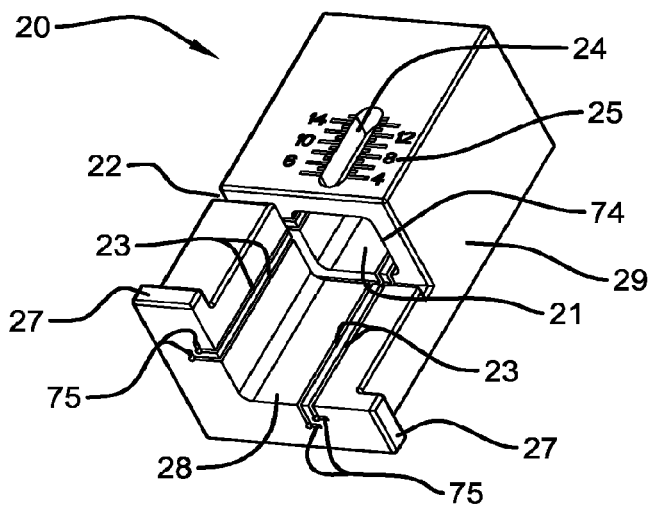
FIG. 5 is an isometric view of the cutting block, in accordance with an aspect of the present invention.

FIGS. 4 and 5 further show for example purposes only, two trimming channels 23 generally disposed within at least two inner walls of bore 21 and the two remaining body walls of cutaway 28. Trimming channels 23 are oriented substantially parallel to bore 21 and typically extend the entire length of body 29, creating distinct exit points 75 at both ends of body 29. Cross-section size indicia corresponding to the resultant cross-sectional dimensions of the osteochondral graft produced by trimming channels 23 may also be disposed near the ends of body 29 to ensure user identification. The structural configurations of trimming channels 23 will correspond to those of angled blade 44 with the respective dimensional tolerances allowing angled blade 44 to be inserted into trimming channels 23 without encountering any interference difficulties.

Figure 7A:
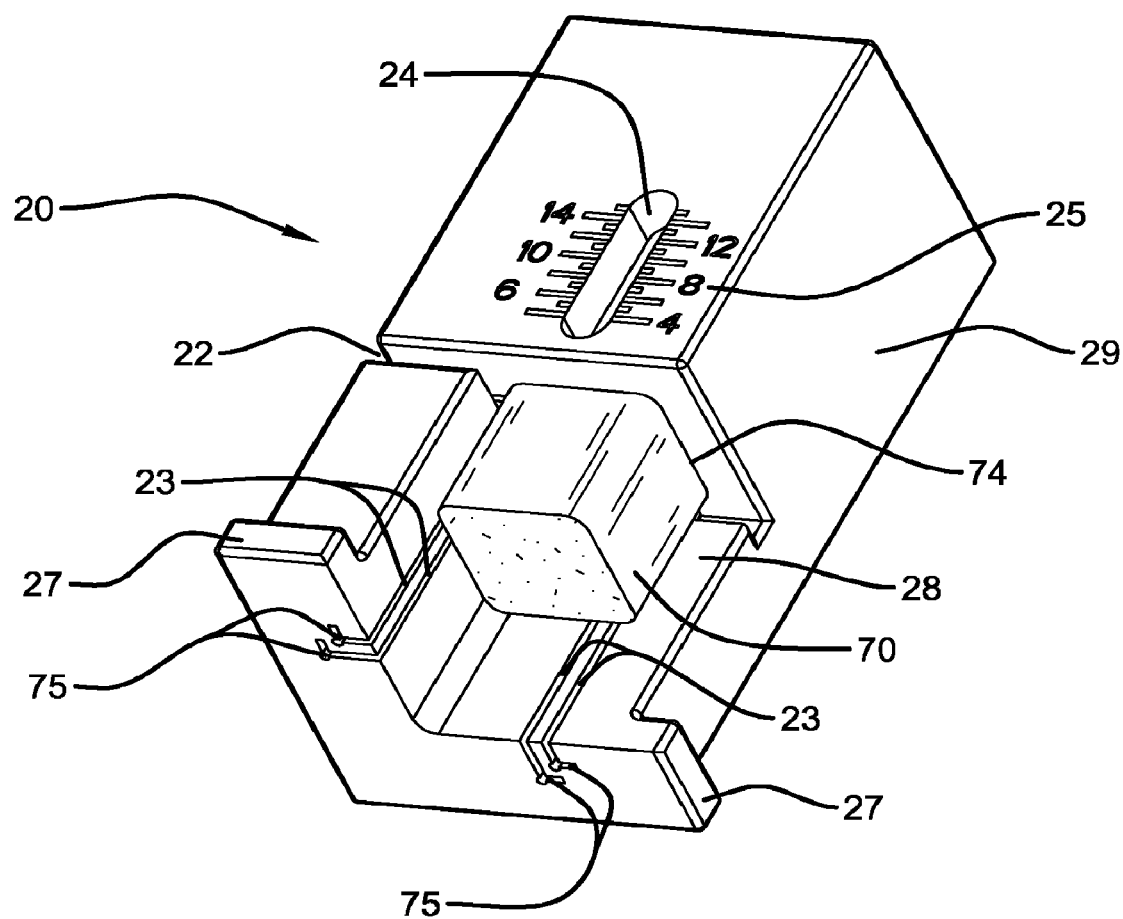
FIG. 7A is an isometric view of the cutting block of FIG. 5 shown with an osteochondral plug inserted into a longitudinal bore, in accordance with an aspect of the present invention.
Figure 7B:
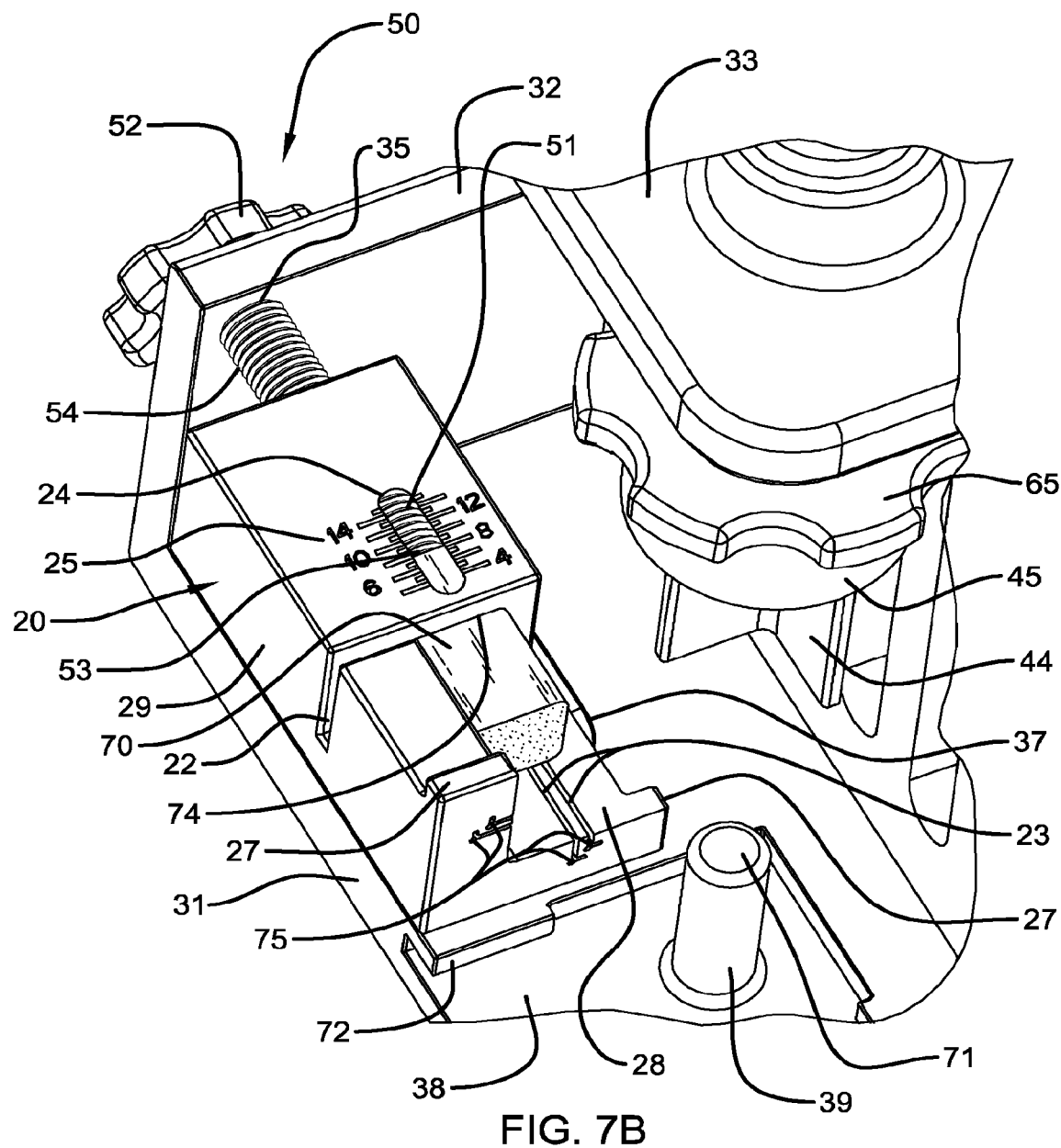
FIG. 7B is an enlarged partial isometric view of the cutting instrument of FIG. 3 shown with the cutting block positioned in the first orientation with the rod mechanism adjusting the position of the inserted osteochondral plug relative to a paring slot, in accordance with an aspect of the present invention.
Figure 7C:
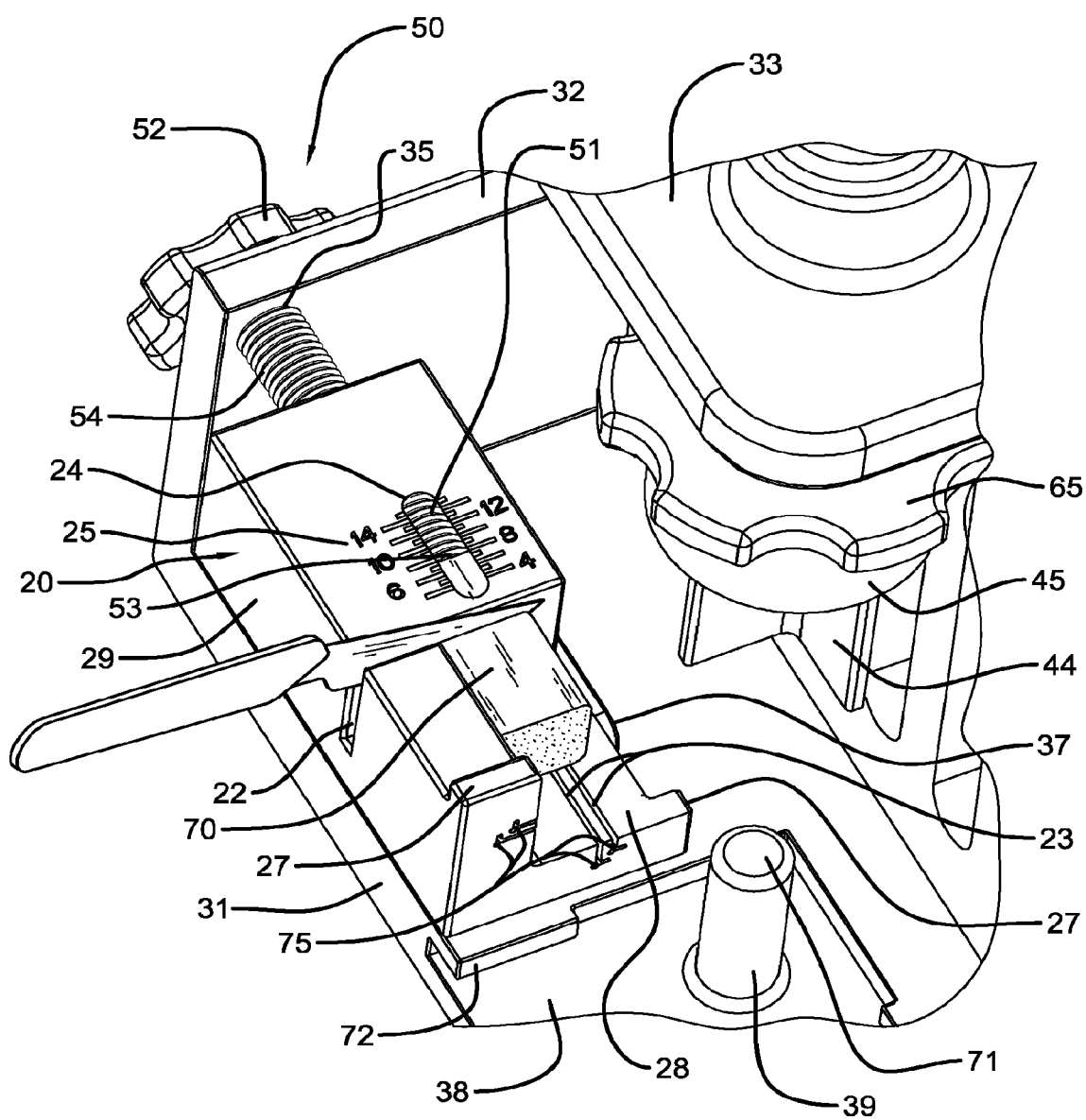
FIG. 7C is an enlarged partial isometric view of the cutting instrument of FIG. 7B shown with a cutting blade inserted into the paring slot of the cutting block to pare the osteochondral plug to a predetermined length, in accordance with an aspect of the present invention.
Figure 7D:
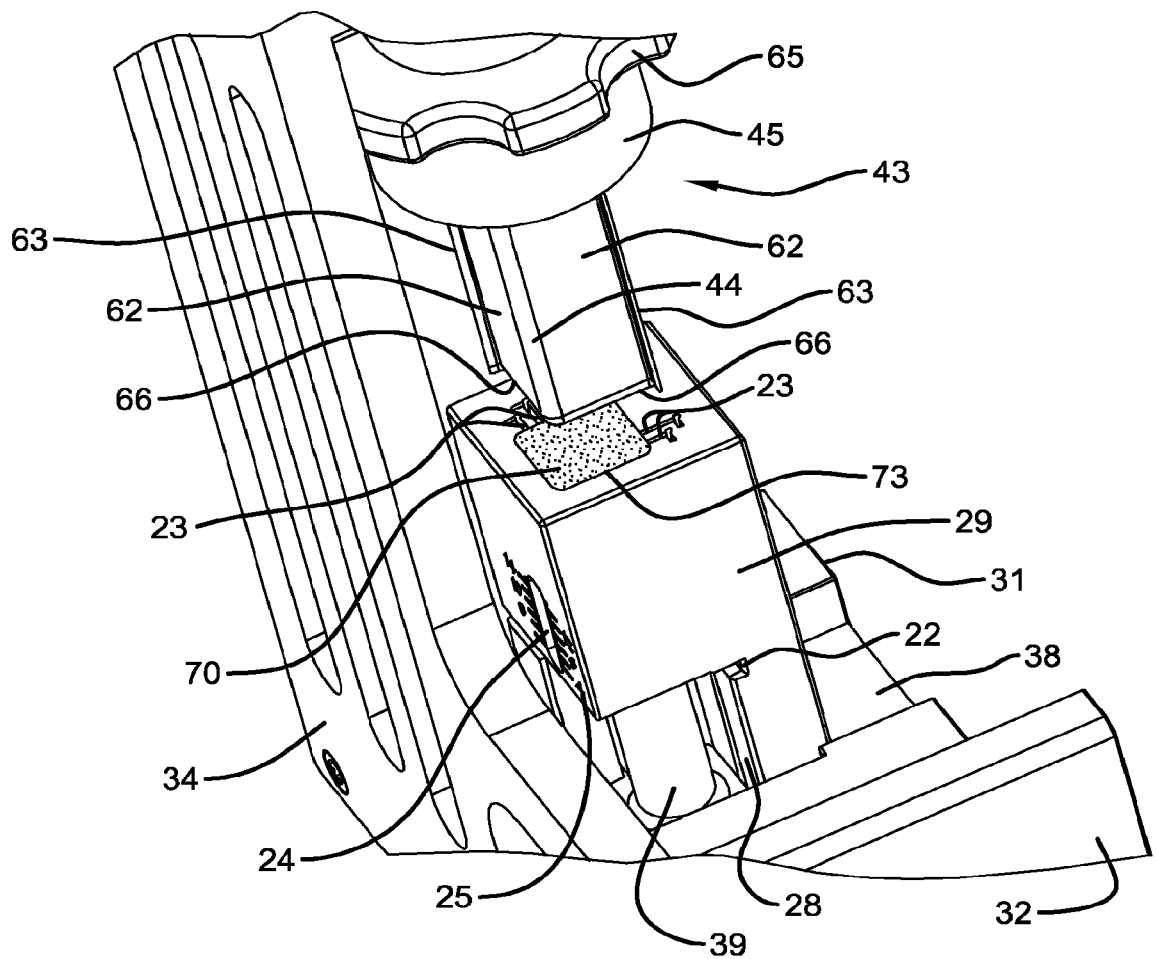
FIG. 7D is an enlarged partial isometric view of the cutting instrument of FIG. 4 shown with the cutting block, including the inserted osteochondral plug, following repositioning in the second orientation relative to the base holder, in accordance with an aspect of the present invention.
Figure 7E:
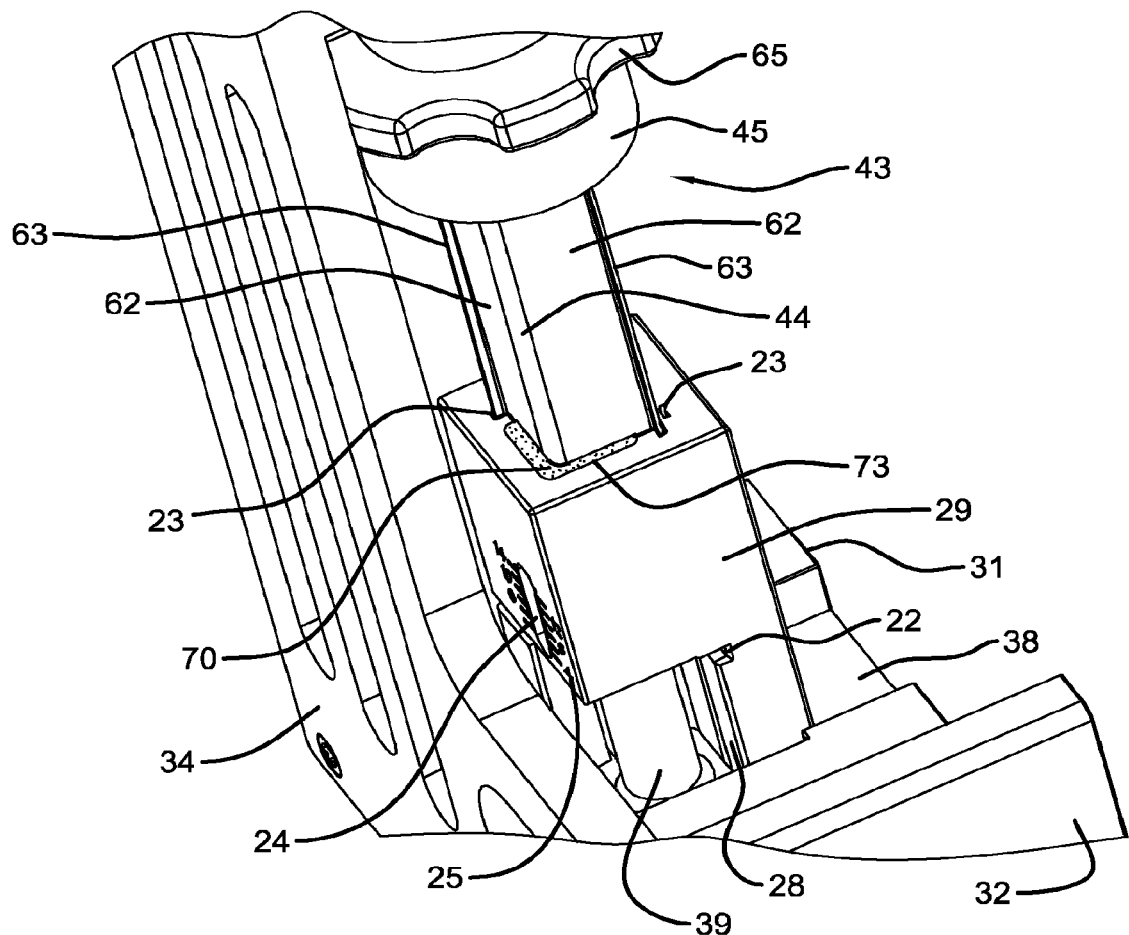
FIG. 7E is an enlarged partial isometric view of the cutting instrument of FIG. 4 shown with the cutting block in the second orientation and an angled blade engaging a trimming channel of the cutting block following the actuation of the trimming mechanism relative to the base holder, in accordance with an aspect of the present invention.

As seen in FIG. 7E, exit points 75 of trimming channel 23 are shaped to receive angled blade 44 and corresponding flanges 63 when trimming mechanism 40 is actuated to cut the osteochondral graft. It should be understood to those skilled in the art that single, or alternatively, multiple trimming channels 23 may be incorporated into a single cutting block 20. Determination of the number of trimming channels 23 provided in cutting block 20 will generally depend upon the user preference.

FIG. 2 shows the two orientations contemplated for cutting block 20 to be positioned relative to base holder 30 during use in cutting instrument 10. The first orientation of cutting block 20 is generally horizontal and parallel to base plate 31. (see FIG. 3). Orienting cutting block 20 in this first position allows the user to employ rod mechanism 50 for paring the length of the osteochondral graft. The second orientation of cutting block 20 is generally vertical and perpendicular to base plate 31. (see FIG. 4.) Orienting cutting block 20 in this second position allows the user to utilize trimming mechanism 40 for cutting the cross-sectional profile of the inserted osteochondral graft.

The general steps of the method for using cutting instrument 10 when preparing an osteochondral graft for implantation are shown at FIGS. 7A-E. Initially, the user may obtain from a tissue bank a pre-shaped graft. The method includes obtaining cutting instrument 10, that generally consists of dual function cutting block 20, the specific structural features of which have been fully describe above herein. Cutting instrument 10 further includes base holder 30 which is configured for engaging cutting block 20 in a first orientation and a second orientation. While in these positions, cutting block 20 functions to hold the osteochondral graft in a manner to facilitate the operation of rod mechanism 50 and trimming mechanism 40, respectively. Cutting instrument 10 also may include rod mechanism 50 that operates to move in a controlled manner, the osteochondral graft within bore 21 of cutting block 20 for the purpose of length paring. Further, cutting instrument 10 has trimming mechanism 40 that functions to cut the osteochondral graft to a pre-determined cross-sectional size and profile by trimming at least two sides of the osteochondral graft utilizing angled blade 44 via a single action cutting motion.

As shown in FIG. 7A, the method for preparing an osteochondral graft for implantation includes inserting through inlet 73 (not shown) osteochondral plug 70 within bore 21 of cutting block 20. As seen in FIG. 7B, cutting block 20 may then be positioned in a first orientation relative to base holder 30 resulting in axial alignment with rod mechanism 50, the structural features of which have been fully describe above herein. As depicted in FIG. 7B, threaded rod 51 is threaded by rotating knob 52, that results in translational movement of threaded rod 51 into horizontal threaded hole 35 positioned through side bracket 32 of base holder 30. Plug pusher end 53 of threaded rod 51 contacts osteochondral graft and pushingly moves the graft within bore 21. As plug pusher end 53 is advanced by continued rotation of knob 52, osteochondral plug 70 is axially maneuvered relative to paring slot 22 and length indicia 25 disposed adjacent to measurement port 24. The user continues to advance pusher plug end 53 and contacted osteochondral plug 70 until one end of the graft is positioned adjacent to the desire length marking which corresponds to the depth of the host site in which the osteochondral graft will be implanted.

Following final positioning of the osteochondral plug 70 relative to paring slot 22, the method further includes paring or cutting osteochondral plug 70 to the length indicated by the aligned length indicia 25. FIG. 7C illustrates the user utilizing a cutting instrument or scalpel blade inserted into paring slot 22 to cut the unneeded length of material from one end of the graft.

The method may further include the user removing cutting block 20 from the substantially horizontal first orientation and repositioning cutting block 20 to a substantially vertical second orientation relative base plate 31 of base holder 30. To ensure proper positioning and accurate alignment of cutting block 20 relative to trimming mechanism 40 in the second orientation, body 29 is positioned to allow access cutaway 28 to face trimming post 39 while alignment tabs 27 are slid into alignment slot 38 formed on the top surface of base plate 31. As shown in FIG. 7D, final positioning of alignment tabs 27 with corresponding retention lips 72 will generally confirm that the second orientation of cutting block 20 has been achieved. Obtaining accurate alignment of cutting block 20 relative to trimming mechanism 40 is paramount to facilitating the cutting of at least two sides of inserted osteochondral plug 70.

Following positioning of cutting block 20 in its second orientation, the method of preparing an osteochondral graft for implantation may provide further for the actuation of trimming mechanism 40 causing a single action cutting motion of angled blade 44 into trimming channels 23 of cutting block 20 resulting in the trimming of at least two sides of osteochondral plug 70 located within bore 21 of cutting block 20. For brevity purposes, all of the structural features of trimming mechanism 40 will not be recited again as these have been fully describe above herein. As seen in FIG. 7E, when threaded rod 41 is threaded into bushing assembly 61 angled blade 44 moves in a downward direction and slides into trimming channels 23 of cutting block 20. To eliminate cutting member 62 deflection or lateral displacement when cutting through the sides of osteochondral plug 70, flanges 63 are disposed along the length of outside edges 67 to provide structural rigidity. Because flanges 63 are integral to cutting members 62, these also will enter corresponding openings that are continuous with trimming channels 23 when threaded rod 41 is advanced.

The predetermined cross-sectional size and shape of the osteochondral graft is obtained following the complete passage of cutting edge 66 of angled blade 44 through the graft positioned within bore 21 and protruding through exits points 75. As disclosed previously herein, the single action cutting motion of trimming mechanism 40 is beneficial in that it minimizes collateral tissue damage to osteochondral plug 70, while angled blade 44 produces a more accurate and definitive cut, thus resulting in the graft cross-section being more closely dimensioned to the cross-section of the prepared host site and therefore increasing the probability of bio-ingrowth between the implanted osteochondral graft and host remaining subchondral bone. It is noted that it should be well understood to those skilled in the art that the sequence of using rod mechanism 50 and trimming mechanism 40 may be reversed from that described herein. The order of preparing an osteochondral graft for implantation will ultimately be determined by the operating surgeon during the course of surgery.

Following the cross-sectional trimming of the osteochondral graft, generally the method will provide for the removal of cutting block 20 from base holder 30. The now properly sized osteochondral graft may then be removed from bore 21, and if necessary, further prepared in some manner, or alternatively, readied for implantation into the host defect site.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method of preparing an osteochondral plug for implantation, the method comprising:
   obtaining a cutting instrument comprising:
      a dual function cutting block having a first end and a second end with a longitudinal bore sized to receive an osteochondral plug extending at least partially therebetween, with a paring slot formed intermediate the first end and second end and transverse to the longitudinal bore for receiving a cutting blade, wherein the dual function cutting block further comprises at least one trimming channel for receiving a trimming mechanism, the trimming channel extending from the first end to the second end of the dual function cutting block and being substantially parallel to the longitudinal bore, wherein the dual function cutting block functions to hold the osteochondral plug within the longitudinal bore to allow for length sizing and cross-sectional sizing of the osteochondral plug;
      a base holder configured for engaging the dual function cutting block in both a first orientation and a second orientation to facilitate the functions of the dual function cutting block;
      a rod mechanism for adjusting the position of the osteochondral plug in the longitudinal bore relative to the paring slot when the dual function cutting block is positioned in the first orientation and the osteochondral plug is positioned within the longitudinal bore, wherein the rod mechanism comprises a threaded rod having a first end and a second end, the second end being configured to contact the osteochondral plug when the osteochondral plug is positioned within the longitudinal bore, wherein the threaded rod, when actuated, engages the base holder resulting in corresponding translational movement of the second end of the rod mechanism, thereby adjusting the position of the osteochondral plug within the longitudinal bore of the dual function cutting block relative to the paring slot; and
      a trimming mechanism for performing cross-sectional sizing of the osteochondral plug by cutting the osteochondral plug to a predetermined cross-sectional size to fit within a bone defect site when the osteochondral plug is located within the longitudinal bore, wherein the trimming mechanism is attached to the base holder and aligned with the longitudinal bore of the dual function cutting block and the at least one trimming channel when the dual function cutting block is positioned in the second orientation, so when actuated, at least one cutting member of the trimming mechanism is translated within the at least one trimming channel to cut the osteochondral plug to a predetermined cross-sectional size;
   inserting the osteochondral plug into the longitudinal bore of the dual function cutting block at the first end of the dual function cutting block;
   positioning the dual function cutting block in the first orientation;
   slidingly translating the inserted osteochondral plug relative to the paring slot by threadably advancing the rod mechanism relative to the base holder and the dual function cutting block; and
   paring the osteochondral plug to a predetermined length by use of a cutting blade inserted into the paring slot.

2. The method of claim 1, further comprising the operator removing the dual function cutting block from the first orientation in the base holder and repositioning the dual function cutting block in the second orientation in the base holder, wherein the dual function cutting block functions to hold the osteochondral plug within the longitudinal bore to allow for cross-sectional sizing of the osteochondral plug.

3. The method of claim 2, wherein positioning the dual function cutting block with the inserted osteochondral plug in the second orientation aligns the at least one trimming channel with the trimming mechanism to facilitate the cutting of at least two sides of the osteochondral plug to a predetermined cross-sectional size while the osteochondral plug is positioned within the longitudinal bore of the dual function cutting block.

4. The method of claim 1, wherein the trimming mechanism further comprises a second threaded rod having a first end and a second end with a rod axis therebetween, a handle being coupled to the first end of the second threaded rod and a cutting assembly, the cutting assembly being rotatably coupled to the second end of the second threaded rod, wherein when the trimming mechanism is in use, rotation of the handle causes the second threaded rod to threadingly engage the base holder resulting in corresponding axial translational movement of the cutting assembly along the rod axis.

5. The method of claim 4, wherein the cutting assembly further comprises an angled blade member rigidly fixed to a connector member with the connector member being detachably coupled to the second end of the second threaded rod, wherein the angled blade is fabricated from at least one of a plastic, a polymer or a metal alloy, and is comprised of at least two cutting members angularly joined along a first edge, the at least two cutting members each having a second edge and a flange disposed along the length of the second edge, wherein the dual function cutting block is configured to receive the flange when the trimming mechanism cuts the osteochondral plug positioned within the longitudinal axis of the dual function cutting block.

6. The method of claim 5, further comprising trimming the osteochondral plug by actuating the trimming mechanism with the dual function cutting block in the second orientation in the base holder to cause the angled blade to enter into the at least one trimming channel and cut the osteochondral plug, located within the longitudinal bore of the dual function cutting block to a predetermined cross-sectional size by cutting at least two sides of the osteochondral plug.

7. The method of claim 6, wherein after the paring and trimming steps are performed, the properly sized osteochondral plug is removed from the longitudinal bore of the dual function cutting block for implantation into a bone defect site.

* * * * *